(12) United States Patent
Grenier et al.

(10) Patent No.: US 8,927,028 B2
(45) Date of Patent: Jan. 6, 2015

(54) PHARMACEUTICAL COMPOSITION CONTAINING COATED, FLOATING PARTICLES

(75) Inventors: Pascal Grenier, Kappelen (FR); Julien Taillemite, Huningue (FR); Severine Serreau, St. Louis (FR); Alain Nhamias, Bartenheim (FR)

(73) Assignee: Jagotec AG, Muttenz (CH)

( * ) Notice: Subject to any disclaimer, the term of this patent is extended or adjusted under 35 U.S.C. 154(b) by 1727 days.

(21) Appl. No.: 11/793,180

(22) PCT Filed: Dec. 15, 2005

(86) PCT No.: PCT/EP2005/013670
§ 371 (c)(1),
(2), (4) Date: Sep. 2, 2008

(87) PCT Pub. No.: WO2006/063858
PCT Pub. Date: Jun. 22, 2006

(65) Prior Publication Data
US 2008/0317841 A1    Dec. 25, 2008

(30) Foreign Application Priority Data
Dec. 15, 2004   (GB) .................................. 0427455.1

(51) Int. Cl.
*A61K 9/48*    (2006.01)
*A61K 9/16*    (2006.01)
*A61K 9/14*    (2006.01)
*A61K 9/20*    (2006.01)
*A61K 31/00*   (2006.01)
*A61K 31/55*   (2006.01)
*A61K 9/00*    (2006.01)
*A61K 9/50*    (2006.01)

(52) U.S. Cl.
CPC ............... *A61K 31/55* (2013.01); *A61K 9/0065* (2013.01); *A61K 9/5073* (2013.01); *A61K 9/5047* (2013.01)
USPC ........... 424/541; 424/464; 424/484; 424/488; 424/490

(58) Field of Classification Search
CPC ... A61K 31/55; A61K 9/0065; A61K 9/5047; A61K 9/5073; A61K 9/4858; A61K 9/5078; A61K 9/0024; A61K 47/36; A61K 9/2054
USPC .......................... 424/451, 464, 484, 488, 490; 514/211.07
See application file for complete search history.

(56) References Cited

U.S. PATENT DOCUMENTS

| | | | |
|---|---|---|---|
| 5,472,712 A | 12/1995 | Oshlack et al. |
| 5,474,786 A | 12/1995 | Kotwal et al. |
| 5,639,476 A | 6/1997 | Oshlack et al. |
| 5,817,338 A | 10/1998 | Bergstrand et al. |
| 6,207,197 B1 | 3/2001 | Illum et al. |
| 6,284,271 B1 | 9/2001 | Lundberg et al. |
| 6,322,819 B1 | 11/2001 | Burnside et al. |

FOREIGN PATENT DOCUMENTS

WO    WO-0158424 A1    8/2001

*Primary Examiner* — Aradhana Sasan
(74) *Attorney, Agent, or Firm* — Mintz Levin Cohn Ferris Glovsky and Popeo, P.C.; Muriel Liberto, Esq.

(57) ABSTRACT

A dosage form exhibiting delayed transit time through the GI tract. The dosage form comprises a plurality of buoyant particles, each comprising an inner drug-containing core, an intermediate layer surrounding said core and a release rate-controlling outer coating.

13 Claims, 1 Drawing Sheet

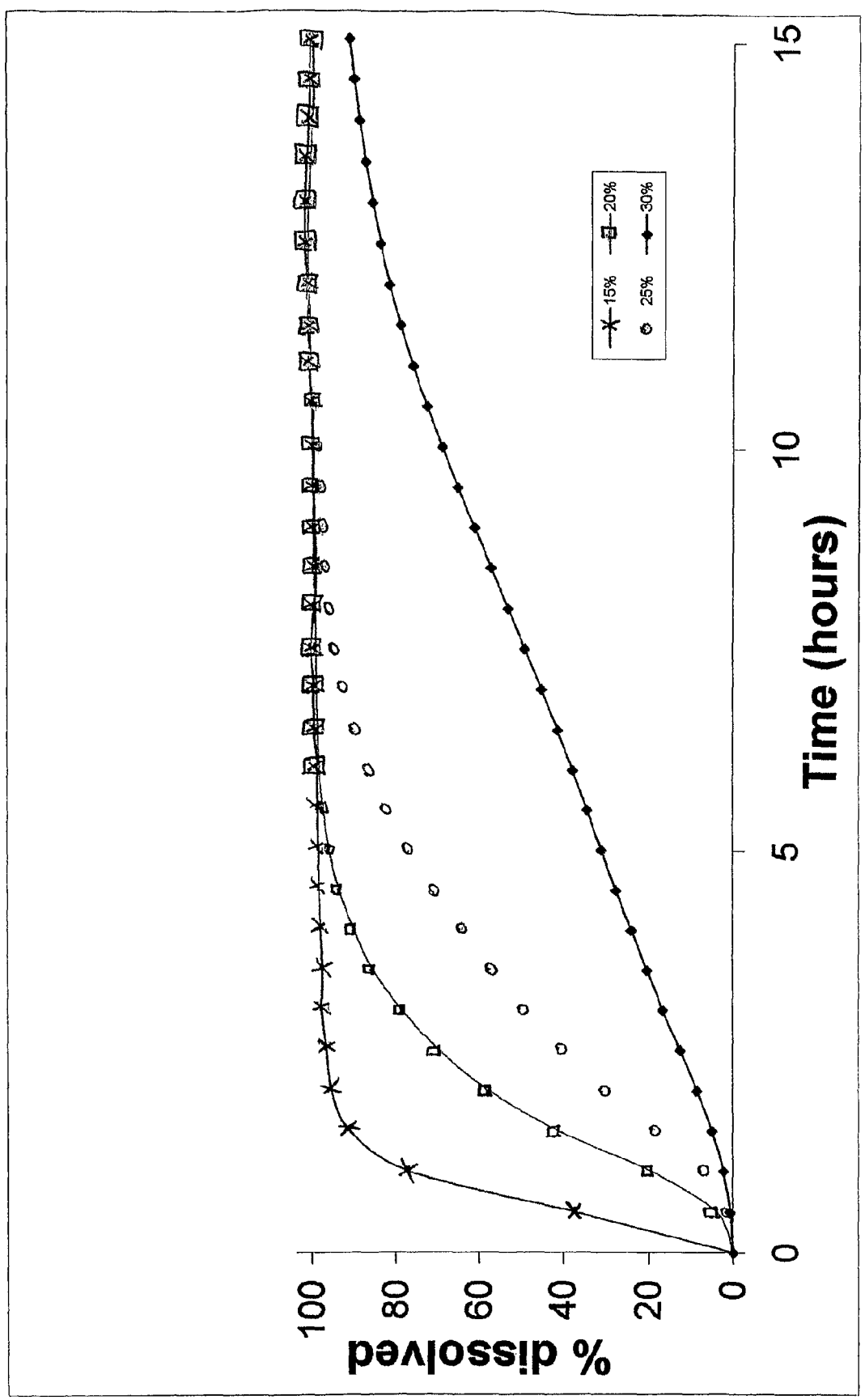

PHARMACEUTICAL COMPOSITION CONTAINING COATED, FLOATING PARTICLES

The present invention is concerned with controlled release dosage forms for the targeted delivery of drugs to the upper part of the gastrointestinal (GI) tract.

RELATED APPLICATIONS

This application is a 35 U.S.C. 371 of PCT/EP/2005/013670, filed on Dec. 15, 2005, which claims priority to UK Application No. 0427455.1, filed on Dec. 15, 2004, all of which are incorporated herein by reference in their entireties.

Dosage forms able to target drug delivery to the upper part of the GI tract are attractive for a number of reasons. In particular, many drugs display better and/or faster absorption at the duodenum or parts of the intestine proximate the duodenum. Furthermore, the absorption gradient for many drugs shows a very steep decline from sites of the intestine proximate the duodenum to areas distal therefrom.

Conventional controlled release dosage forms can exhibit significant variance in bioavailability, particularly if there is a steep absorption gradient along the intestine. Similarly, variable bioavailability might occur if a drug substance is unstable in the intestinal environment. Moreover, because the transit time of a dosage form through the stomach is rapid under fasted conditions as compared with fed conditions, conventional controlled release dosage forms often display marked variance in bioavailability between the fed and fasted states.

As a result, many conventional controlled release dosage forms fail in development because of poor pharmacokinetics, and many potential useful therapies are lost to the public as a result.

Having regard to the foregoing problems, it would be desirable if a dosage form could be held above an optimal site of absorption for an extended period of time in order that a significant amount, preferably all or substantially all, of the drug can be released for absorption at or near this site.

The idea of delaying the transit time of a dosage form through the GI tract as a result of prolonging its gastric residence is known in the art and there have been several approaches previously suggested for achieving this.

One approach relies on a unitary dosage form that is so large that its passage through the duodenal sphincter is restricted. This approach relies on the dosage form expanding in the stomach after ingestion.

A problem with this approach is that the unitary dosage form must reliably swell or expand to prevent its quick passage through the pyloric sphincter. Unless the expansion mechanism is entirely reliable, one could anticipate patient compliance issues and variability in dosing: For example, premature expansion of the dosage form could be very uncomfortable for a patient presented with swallowing difficulties, whereas delayed expansion could result in the dosage form passing through the pylorus without any delay. In fact, in view of the muscular nature of the stomach wall, even dosage forms larger than the pylorus cut-off size can be squeezed through the pylorus under mechanical action.

Another approach relies on the dosage form presenting a mucoadhesive outer coating that adheres to the stomach wall such that it is retained in the stomach for a prolonged period of time. However, a problem with this approach is that the stomach wall is not rigid. The wall is subject to propulsive motor activity. Further, there is a large secretory activity of the stomach mucosa. Still further, the dosage form cannot be attached to the wall with a defined application pressure. As a result, variable residence times in the stomach can be anticipated as a result of unpredictable physiological factors.

An additional problem that is common to all of the foregoing approaches is that formulation requirements necessary to obtain the mucoadhesion, or size expansion, may not be consistent with the formulation releasing the drug with a desired release profile. It stands to reason that there is little point in delaying the transit time of a dosage form if, as a result, drug is released from that dosage form in an uncontrollable or undesired manner.

It has now been found that it is possible to provide dosage forms that exhibit slow transit times through the GI tract, and which also exhibit zero order, or substantially zero order, release kinetics by presenting such dosage forms in buoyant, multiparticulate forms such, for example, as beads or microspheres. Such dosage forms do not require any mucoadhesive outer coating.

According to a first aspect of the present invention therefore there is provided a dosage form comprising a plurality of particles that are buoyant in aqueous media, said particles comprising a drug-containing inner core, an intermediate layer surrounding said core and a drug release rate-controlling coating surrounding said intermediate layer.

Said inner core may comprise at least one matrix-forming polymer and at least one drug. Said at least one matrix-forming polymer may be chosen to be gellable and/or soluble in aqueous media. Examples of suitable matrix-forming polymers include: hydroxyalkyl cellulose, e.g. hydroxypropylcellulose and hydroxypropylmethylcellulose; poly(ethylene)oxide; alkylcellulose, e.g. ethylcellulose and methylcellulose; carboxymethylcellulose; hydrophilic cellulose derivatives; polyethylene glycol; polyvinylpyrollidone; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); carboxyvinyl polymers; polyvinyl alcohols; glucans; scleroglucans; chitosans; mannans; galactomannans; xantan gums; carrageenin; carrageenans; amylose; alginic acid, and salts and derivatives thereof; and poly (vinylacetate).

The nature of the polymer or polymers selected depends upon the desired gellable and/or solubility properties of the matrix; the composition of the inner core can be adjusted to achieve any desired result.

Similarly, the amount of said at least one matrix-forming polymer employed is be influenced by the composition of the inner core, and the desired gellability and/or solubility properties. Generally however, said at least one matrix-forming polymer may be present in amounts of 20 to 90% by weight of the inner core; more particularly 40 to 70% by weight.

Said at least one drug may be dispersed or dissolved within the matrix forming polymer. The at least one drug may be present in an amount of from 0.1 to 80% based on the weight of the dosage form; more particularly from 1 to 50% wt.

Any drug that can usefully be released and absorbed in the stomach, or in regions of the intestine in or near to the duodenum, may be employed in the present invention.

The present invention may be particularly useful for delivering drugs that are poorly absorbed in the lower gastrointestinal tract, but well absorbed in the upper gastrointestinal tract, or drugs that exhibit poor solubility such that the increased retention time in the stomach provided by the dosage forms of the present invention allows for a greater quantity of drug to be delivered from the dosage form than would otherwise occur.

Typically, antiviral, antifungal and antibiotic agents, e.g. sulfonamides, quinolones, penicillins, cephalosporins, aminoglycosides and tetracyclines, are representative classes of agents for which the invention may be particularly useful.

Such antibiotic agents may include, for example, β-lactam antibiotics, vancomycin, clidamycin, erythromycin, trimethoprim-sulfamethoxaazole, rifampin, ciprofloxacin, amoxicillin, clindamycin, ceftriaxone, cefotaxime, chloramphenicol, clindamycin, cefoxitin, doxyclycline, spectinomycin, ofloxacin, rifampin, minocycline, doxycycline, aztreonam, imipenem, meropenem, nitrofurantoin, azithromycin, atovaquone, trimetrexate, dapsone, primaquin, trimetrexate, ketoconazole, floconazole, amphotericin B, itraconazole, trifluridine, foscarnet, zidovudine amantadine, interferon alfa, sulfonamides such as sulfisoxazole, sulfadiazine, and sulfasalazine, quinotones and fluoroquinolones such as, for example, cinoxacin, forfloxacin, diprofloxacin, oflloxacin, spardlosxacin, lomefloxacin, fleroxacin, pefloxacin and amifloxacin, gentamicin, tobramycin, amikacin, netilmicin, kanamycin, and neomycin.

Representative antiviral agents include acyclovir, famciclovir, foscarnet, ganciclovir, idoxuridine, sorivudine, trifluridine, valacylcovir, vidarabine, didanosine, stavudine, zalcitabine, zidovudine, amantadine, interferons, e.g. interfon alpha, ribavirin, rimantadine, nucleoside RT inhibitors such as lamivudine and adeforvir, non-nucleoside inhibitors such as nevrapine, delavairidine, Iviride, saquinavir and indinavir, nucleoside DNAp inhibitors such as famciclovir, fialuridine, cidofovir and lobucavir, antisense oligonucleotides such as afovirsen, receptor decoys such as sICAM-1, capsid binding agents such as pirodavir and neuraminidase inhibitors such as GG167.

Specific examples of drugs that are readily absorbed in the upper gastrointestinal tract relative to the lower gastrointestinal tract are acyclovir, ganciclovir, cimetidine, ranitidine, captopril, methyldopa and selegiline.

Specific examples of drugs that exhibit poor solubility in water are diphenidol, meclizine hydrochloride, prochloperazine maleate, phenoxybenzamine, triethylperazine maleate, anisindone, diphenadione erythrityl tetranitrate, digoxin, isofilurophate, acetazolamide, methazolamide, bendroflumethiazide, chlorpropamide, tolazamide, chlormadionone acetate, phenaglycodoi, allopurinol, alluminurri aspirin, methotrexate, acetyl sulfisoxazole, erythromyciin, progestins, esterogenic, progestational corticosteroids, hydrocortisone, hydrocorticosterone acetate, cortisone acetate, tramcinolone, methyltesterone, 17-beta-estradiol, ethinyl estradiol, prazosin hydrochloride, ethinyl estradiool 3-methyl ether, prednisolone, 17-alpha-hydroxyprogesterone acetate, 19-norprogesterone, norgestrel, norethindrone, progesterone, norgesterone and norethlynodrel.

Retention of the dosage form of the present invention in the stomach for a prolonged period of time may make it especially useful for the localised treatment of gastric acidity and gastrointestinal disorders such as duodenal ulcers, peptic ulcers and chronic gastritis.

Representative drugs for such localised treatments include cimetidine, rantitidine, famotidine, nizatidine, zolentine, omeprazole, lansoprazole and active agents useful for the treatment of *Helicobacter pylori*, such as metronidazole, timidazole, amoxicillin, clarithromycin, minocycline and tetracycline.

The dosage form of the present invention is particularly suited to the administration of drugs against *Helicobacter pylori*, e.g. antibiotics as exemplified by minocycline which are able to penetrate the space between the inner stomach lining and the stomach protective mucous layer where the *Helicobacter pylori* organism is present, with the result of eradicating the *Helicobacter pylori* organism either totally or to such a degree that relapse after treatment for a large portion of the treatment population may be minimised. The increased residence time of the dosage form provided by this invention in the stomach permits a drug delivery period at the situs of the organism that is longer than that provided by conventional tablets and capsules. The increased efficiency and efficacy of treatment afforded by the present invention may allow one to treat gastric disorders in a large number of subjects with dosage forms having a single drug, for example minocycline. Accordingly, more complicated treatment regimens may be avoided.

Other drugs exhibiting a narrow absorption window, preferably in the portion of the gastro intestinal tract adjacent the duodenum, such, for example, as alfluzosine, prazosin, ketanserin, guanabenz acetate, captopril, captopril hydrochloride, enalapril, enalapril maleate, lysinopril, hydralazide, methyldopa, methyldopa hydrochloride, levodopa, carbidopa, benserazide, amlodipine, nitrendipine, nifedipine, nicardipine and verapamil, may be employed in the present invention.

Said inner core may comprise about 10 to 90% by weight of the total dosage form, more particularly about 60% wt.

Said intermediate layer may comprise porous excipients that are water insoluble or poorly water soluble, e.g. hydrophobic, waxy and/or fatty excipients. Such excipients include: any of the known hydrophobic cellulosic derivatives and polymers including alkylcellulose, e.g. ethylcellulose, hydroxypropylcellulose, hydroxypropylmethylcellulose, carboxymethylcellulose and derivatives thereof; polymethacrylic polymers, polyvinylacetate and cellulose acetate polymers; fatty acids or their esters or their salts; fatty alcohols; polyoxyethylene alkyl ethers; polyoxyethylene stearates; sugar esters; lauroyl macrogol-32 glyceryl, stearoyl macrogol-32 glceryl and the like.

Other excipients providing a waxy, hydrophobic quality to the intermediate layer may be chosen from waxy substances such as carnauba wax, paraffin, microcrystalline wax, beeswax, cetyl ester wax and the like; non-fatty hydrophobic substances such as calcium phosphate salts, e.g. dibasic calcium phosphate may also be employed. Preferred ingredients for use in the intermediate layer include glyceryl behenate and dibasic calcium phosphates.

The aforementioned excipients may provide from 50 to 100% by weight of the constituents of the intermediate layer; more particularly from 80 to 100% wt.

The intermediate layer preferably comprises from 50 to 80% by weight of the dosage form, more particularly about 70% wt., and may serve to provide the microspheres with all or at least a substantial part of their buoyancy in aqueous media.

Said outer coating may comprise a film-forming polymer. Said film-forming polymer may be selected from any of those film-forming polymers known to those skilled in the art to be release-rate controlling. A characteristic of the outer coating is that it preferably comprises at least one water-insoluble polymer. Typical of such a polymer is alkylcellulose; more particularly ethylcellulose. Suitable ethylcellulose polymers include those available under the trade name SURELEASE®, e.g. SURELEASE® E7-19070, available as a plasticised aqueous dispersion with oleic acid and medium chain triglyercides from Colorcon Limited, Dartford, UK. Other suitable ethylcellulose polymers include the various polymers known and available as film-forming polymers under the ETHOCEL® marks (Anstead International, Basildon, UK).

Other release rate-controlling film-forming polymers may also be employed, such as methacrylic acid methacrylic acid ester copolymers. The Eudragit® (Röhm GmbH & Co. KG, Darmstadt, Germany) coating polymers are a family of methacrylic copolymers, and those release rate-controlling members are useful in dosage forms of the present invention, e.g. the non-pH dependant RL 30D [poly(ethyl acrylate-co-methyl methacrylate-cotrimethylammonioethyl methacrylate chloride)] and RS 30D [poly(ethyl acrylate-co-methyl methacrylate-cotrimethylammonioethyl methacrylate chloride)] grades.

Given that the outer coating comprises a water-insoluble polymer, the ability and extent to which the outer coating controls the rate of release of active substance may depend on the thickness of said outer coating, as this in turn will affect the rate of ingress of moisture through the coating, and the rate of egress of drug substance. Said rate of release may be proportional to the thickness of said outer coating.

The thickness of said outer coating may be influenced by the amount of film-forming polymer employed. Preferably, the outer coating may employ at least one film-forming polymer in amounts of about 10 to 90% by weight based on the total weight of the dosage form.

The rate of release of drug through the coating may be influenced by the packing of the polymer chains, drug being able to be released through interstitial spaces in the polymer matrix. However, drug release rate can also be affected by the inclusion of small amounts of water-insoluble or water-soluble substances in the outer coating. Water-soluble substances may be washed out of the outer coating to form pores or channels through the insoluble polymer through which drug substance can pass. Water-soluble excipients for this purpose are well known in the art, and include well-known pore and channel formers such as lactose, HPMC, mannitol, sugars and the like. The water-insoluble excipients for this purpose may act by disrupting the polymer matrix, creating faults therein through which drug substance can pass. Water-insoluble excipients for this purpose are well-known in the art and include such materials as talc, dicalcium phosphate and the like. The amount of such excipients may vary between 1 and 50% by weight based on the weight of the outer coating, depending on the desired release rate.

The outer coating may be applied directly to the intermediate layer, but in some embodiments the intermediate layer may have an irregular surface; for example it may be pitted with cracks, fissures or the like as a result of the manufacturing process. When an outer coating is applied directly to such an irregular surface, the depth of coating at different points on the dosage form is likely to vary somewhat. This variance of outer coating thickness may have a deleterious effect on the rate of release of a drug substance from the dosage form.

In a preferred embodiment the dosage form contains a film coating disposed between said intermediate layer and said outer coating. The film coating's primary function is to present a smoother surface on which said outer coating may be applied in order to ensure maximal uniformity of the thickness of the outer coating. Suitable materials for inclusion in the film coating include such film-forming polymers as are known in the art for use in aesthetic coatings, by which is meant any of those film-forming polymers used to coat dosage forms to give them a smooth and/or glossy finish.

Such film coatings may comprise at least one hydroxypropylmethylcellulose polymer of the kind typically employed in film coatings. In particular the OPADRY® hydroxypropylmethylcelluloses available from Colorcon Limited, Dartford, UK may be employed, especially OPADRY® YS-1-7003. Other polymers such, for example, as polyvinylalcohol, e.g. OPADRY® AMB type, and waxy polymer coatings such, for example, as the OPAGLOS® type may also be employed. Alternatively, a sugar coating could be employed as a film-forming layer, alone or in combination with other aforementioned film forming polymers.

When employed, the film coating may be present in an amount of 1 to 80% by weight based on the total weight of the formulation; more preferably 3 to 10% wt.

Preferably the outer coating does not contain any component that is mucoadhesive, i.e. it does not contain—or is substantially free of—any excipient the purpose or function of which is to stick to the stomach mucosa and thereby delay transit of the dosage form through the stomach.

The dosage form of the present invention may contain one or more additional excipients that are conventionally employed in the formulation of solid oral dosage forms, e.g. diluents and fillers which add bulk to a formulation and enable dosage forms of desired size and shape to be formed, binders which promote the adhesion of constituent particles of a formulation to maintain its integrity, colourants, flavourants and preservatives.

The dosage form of the present invention is presented as a solid oral dosage form. In some embodiments it may be presented as a capsule containing a plurality of beads. Alternatively, said particles may be compressed with commonly available tablet excipients to form a compressed dosage form. In yet another embodiment the particles may be contained in a sachet form.

The size of the particles may depend upon the process(es) used to form them and the conditions employed in such processes. However, particles having a diameter of at least about 0.1 mm and up to about 2 mm are desirable and can easily be prepared using a method described below for example. In some embodiments at least 90% wt. of the particles may have an effective diameter of at least 0.1 mm but no more than 2 mm. Where the particles are spherical then their effective diameter is their actual diameter, but for non-spherical particles the "effective diameter" may be determined using reticulated screens or meshes having known pore sizes.

The particles of the dosage form of the present invention are of low density. Such low density may contribute to the slow transit time of the dosage form. By "low density" here is meant that the particles may have an average density of about 1 g/cm$^3$ or less. In some embodiments at least 90% wt. of the particles, preferably at least 95% wt., have a density of about 1 g/cm$^3$ or less. As mentioned above, the particles according to the present invention are buoyant. For example, when placed in a beaker containing still aqueous media, e.g. water, the particles may float on the surface of such medium for a period in excess of twelve hours. It will be appreciated that gastric fluid may have a density that is greater than that of water, and furthermore the GI tract presents a turbulent environment in which particles may be continually displaced. Accordingly, in some embodiments, the particles may be slightly more dense than water, but still have the requisite buoyancy in gastric media for the purposes of the present invention. Thus, said particles may have an average specific gravity (relative to water) of up to about 1.1, and preferably at least 90% wt., more preferably 95% wt., of the particles have an individual specifica gravity of about 1.1 or less.

The dosage form of the present invention may dissolves in aqueous media to release a drug substance with a release profile that is zero order or substantially zero order. By "zero order" here is meant that the rate of release of the drug is constant over time. Desired release profiles, whereby at least 80% wt. of the drug is released with zero order or substantially zero order, may be obtained with the dosage form of the present invention.

Release profiles may be measured using the compendial test methods and apparatus (See for example the U.S. Pharmacopeia ("USP") 26 National Formulary ("NF") 21 "771 Dissolution Test"). A test described therein is the USP Method II (the so-called "Paddle Method"). Dissolution data and release profiles can be obtained using these methodologies, albeit with some modification in dissolution medium having regard to the nature of the drug substance. In a medium consisting of 600 ml of a 50 mM acetate buffer at pH 4.5 and a paddle speed of 100 rpm, 80% wt. of drug release may occur within 2 to 12 hours, depending on the thickness of the outer coating.

The particles may be modified to achieve other drug release profiles. For example, the particles may be over-coated with an additional drug-containing layer to obtain pulsatile delivery, whereby the drug in said over-coated layer (which may be the same or different from the drug(s) within the particles) is released according to a first release profile, and said drug or drugs within the particles are released according to a second release profile.

Additionally or alternatively, the particles may be over-coated with an enteric coating to delay release of drug substance.

Modification of the release profile of drug from the particles may also be achieved by means of an encapsulating medium surrounding the particles. In particular, a capsule or tablet containing the particles may be adapted to delay or retard the release of the drug or drugs from the particles. In some embodiments said tablets or capsules may contain or carry a drug substance externally of the particles, which drug substance may be released with a first release profile before the drug or drugs are released from the particles according to a second release profile.

The dosage form of the present invention may find utility in the treatment or prevention of disease states in mammals depending on the drug or drugs that are employed. For the above-mentioned lists of drugs, the disease states that may be treated or prevented are those against which such drugs are known to be effective.

The amount of drug that may be employed in the dosage form may depend upon the drug used, the disease state(s) to be treated and the condition of the patient, but it may be in the range of 0.01 mg to 1 g. By way of example, suitable daily doses are in the range of 0.01 mg to 5 g, depending on the drugs to be employed.

The dosage form may be dosed once or more times daily depending on the condition(s) to be treated.

According to a further aspect of the invention there is provided a method of treatment or prophylaxis of a disease state which comprises administering to a patient in need of such treatment or prophylaxis a dosage form according to the present invention, said dosage form including at least one drug that is effective against said disease state.

The dosage form of the present invention has the advantage that it may deliver said at least one drug to specific absorption sites of the GI tract in mammalian subjects. Moreover, given that the dosage form is presented in multiparticulate form, variability in the dosing is likely to be ameliorated: In the event of one of the particles failing to exhibit a prolonged gastric residence time, only a small fraction of the total delivered dose would be delivered to the patient in an uncontrolled manner.

The dosage form of the present invention may have the additional advantage that it can be prepared using established pharmaceutical processing methods with materials that are approved for use by the relevant pharmaceutical regulatory authorities.

A method of preparing the dosage form of the present invention provides yet another aspect of the invention. Said inner core may be built up using a fluid bed drier equipped with a rotogranulator insert according to techniques known in the art. Alternatively, extrusion spheronisation techniques may be employed.

Said intermediate layer may be built up using a fluid bed drier equipped with a rotogranulator insert according to techniques known in the art.

Said coating step(s) may be carried out using conventional film-coating techniques in a fluidized bed apparatus.

An assemblage of inner cores may be formed by charging a rotogranulator (e.g. a Glatt GPCG1 fluid bed dryer, Glatt GmbH, Weimar, Germany) with the constituents of the inner core in powder form. The bed of powder may then be set in centrifugal motion, and a binding solution, e.g. an aqueous solution of PVP, entered into the rotagranulator tangentially; the core particles may be built up in a manner known per se.

Said intermediate layer may be applied to said inner cores in a rotogranulator. The inner cores may be fluidized in a rotogranulator equipped with an ACCURATE® system (Accu-Rate, Inc., Whitewater, Wis., USA). Binding solution and the constituents of said intermediate layer in powder form may be fed into the rotogranulator, such that the intermediate layer is built up in a manner known per se.

The inner cores coated with said intermediate layer may then be transferred to a fluid bed drier, and the coating or coatings applied according to techniques known in the art; for example, said fluid bed drier may be equipped with Wurster cylinder.

There now follows are series of examples that serve to illustrate the present invention with reference to the accompanying drawing in which the sole FIGURE is a graph of the release profiles of four different formulations in accordance with the invention.

Example 1

| Inner core | mg | % |
| --- | --- | --- |
| Diltiazem HCl | 60 | 2.78 |
| Methocel ® K100M | 180 | 8.35 |
| Avicel ® PH102 | 120 | 5.57 |
| Compritol ® 888ATO | 240 | 11.14 |
| Plasdone ® K29-32 | 29.3 | 1.36 |

| Intermediate layer | | |
| --- | --- | --- |
| Methocel ® K100M premium | 709.53 | 32.92 |
| Compritol ® 888 ATO | 709.53 | 32.92 |
| Plasdone ® K29-32 | 106.77 | 4.95 |

| Outer Coating | | |
| --- | --- | --- |
| Opadry ® YS-1-7003 | 215.51 | 10.00 |
| Surelease ® E7-19070 | 431.00 | 20.00 |

Diltiazem HCl, Methocel® K100M, Avicel® PH102 and Compritol® 888ATO are sieved and added to a rotogranulator (GPCG1, Glatt) to form a powder bed. The powder bed is set into centrifugal motion and a binder solution consisting of 5% w/w solution of Plasdone® K29-32 in water is fed into the rotogranulator as a tangential spray. The inner cores thus formed are dried by feeding hot air at a temperature of 65° centigrade into the granulator until the cores reach a temperature of 35° centigrade.

The inner cores formed above now form a powder bed which is set in centrifugal motion in the rotogranulator equipped with an ACCURATE® system. The powder constituents of the intermediate layer are fed into the granulator tangentially using the ACCURATE® system, as is the binder solution (consisting of 5% w/w Plasdone® K29-32 in water). The intermediate layer is built up in this manner, and the particles are dried in a similar manner to that described above.

The particles thus formed are transferred to a fluidized bed drier equipped with a Würster Cylinder. The particles are fluidized by an air flow passing up through the base plate of the drier and the coating solution is fed into the drier in a direction concurrent with the air flow. The coated particles are dried in an air flow at 60° centigrade until the they reach a temperature of no more than 40 to 42° centigrade to provide an assmeblage of coated particles forming a dosage form in accordance with the present invention.

Example 2

To determine the in vitro release characteristics of the formulation described above and additional formulations substantially the same as the formulation described above differing only in the quantities of Surelease® ethylcellulose in their outer coatings (15% wt., 25% wt. and 30% wt.), standard equipment was used as defined and described in United States Pharmacopoeia USP XXIII, chapter 711, page 1792, paragraph "Apparatus 2". This equipment had a stirring paddle comprising a blade and a shaft and was operated at 100 rpm. Dissolution was investigated at 37° centigrade in 600 ml of a dissolution medium made up of 0.1 M acetate buffer of pH 4.5. The release of the active substance was monitored by UV spectrophotometry at 278 nm.

The results are illustrated in the accompanying FIGURE as respective time profile diagrams for the four formulations.

For each formulation the following was observed on the in vitro release characteristics:

The first release of active substance takes place within a release period of less than one hour.

By adjusting the outer coating coat weight it is possible to modulate the release rate such that at least 80% wt. of drug is released between 1 hour and about 15 hours. Furthermore, release of at least 80% wt. of drug is achieved with substantially zero order kinetics.

The invention claimed is:

1. A dosage form comprising a plurality of particles that are buoyant in aqueous media, each particle comprising:
   a drug-containing inner core;
   an intermediate layer surrounding the core comprising at least one water-insoluble or poorly soluble porous excipient, said layer comprising from 50% to 80% by weight of the dosage form and providing buoyancy to said particles in aqueous media; and
   a drug release rate-controlling outer coating;
   and a film coating disposed between said intermediate layer and said drug release rate-controlling outer coating,
   wherein the particles have an average density of 1 g/cm$^3$ or less.

2. The dosage form according to claim 1, wherein said inner core comprises at least one matrix-forming polymeric material and at least one drug.

3. The dosage form according to claim 2, wherein said at least one matrix forming polymer is selected from: hydroxypropylcellulose and hydroxypropylmethylcellulose; poly(ethylene)oxide; ethylcellulose; methylcellulose; carboxymethylcellulose; hydrophilic cellulose derivatives; polyethylene glycol; polyvinylpyrollidone; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); carboxyvinyl polymers; polyvinyl alcohols; glucans; scleroglucans; chitosans; mannans; galactomannans; xanthan gums; carrageenans; amylose; alginic acid, and salts and derivatives thereof; and poly (vinylacetate).

4. The dosage form according to claim 1, wherein said intermediate layer further comprises at least one waxy or fatty material.

5. The dosage form according to claim 4, wherein said waxy or fatty material is a hydrophobic cellulosic derivative or polymer selected from: ethylcellulose, hydroxypropylcellulose, hydroxypropylmethylcellulose, carboxymethylcellulose and derivatives thereof; polymethacrylic polymers, polyvinylacetate and cellulose acetate polymers; fatty acids or their esters or their salts; fatty alcohols; polyoxyethylene alkyl ethers; polyoxyethylene stearates; sugar esters; lauroyl macrogol-32 glyceryl, stearoyl macrogol-32 glceryl; carnauba wax, paraffin, microcrystalline wax, beeswax, cetyl ester wax; non-fatty hydrophobic substances such as calcium phosphate salts and glyceryl behenate.

6. The dosage form according to claim 1, wherein said outer coating contains a release rate-controlling polymer.

7. The dosage form according to claim 6, wherein said release rate-controlling polymer is selected from ethylcellulose and methacrylic acid-methacrylic acid ester copolymers.

8. The dosage form according to claim 7, wherein said polymer is selected from ethylcellulose polymers, ethylcellulose film-forming polymers and methacrylic copolymer coating polymers.

9. The dosage form according to claim 1, wherein said coating disposed between said intermediate layer and said drug release rate-controlling outer coating contains at least one polymer selected from hydroxypropylmethylcellulose and polyvinylalcohol.

10. The dosage form according to claim 9, wherein said polymer is selected from PVA (polyvinyl alcohol) type film coating polymers and sodium carboxymethylcellulose, maltodextrin and dextrose monohydrate/shellac, and acetylated monoglyceride type film coating polymers.

11. The dosage form according to claim 9 in the form of a compressed tablet, capsule or sachet comprising a plurality of buoyant particles.

12. The dosage form according to claim 9, wherein said at least one drug is selected from drugs that can be released and absorbed or act locally in the stomach or that can be released and absorbed in the portion of the intestine proximate to the duodenum.

13. The dosage form according to claim 12, wherein said at least one drug is selected from: sulfonamides, quinolones, penicillins, cephalosporins, aminoglycosides and tetracyclines; beta-lactam antibiotics, vancomycin, clidamycin, erthromycin, trimethoprim-sulfamethoxaazole, rifampin, ciprofloxacin, amoxicillin, clindamycin, ceftriaxone, cefotaxime, chloramphenicol, clindamycin, cefoxitin, spectinomycin, ofloxacin, minocycline, doxycycline, aztreonam, imipenem, meropenem, nitrofurantoin, azithromycin, atovaquone, trimetrexate, dapsone, primaquin, trimetrexate, ketoconazole, floconazole, amphotericin B, itraconazole, trifluridine, foscarnet, zidovudine amantadine, interferon alfa, sulfonamides selected from sulfisoxazole, sulfadiazine, and sulfasalazine; quinotones and fluoroquinolones selected from cinoxacin, forfloxacin, diprofloxacin, ofloxacin, spardlosxacin, lomefloxacin, fleroxacin, pefloxacin, amifloxacin, gentamicin, tobramycin, amikacin, netilmicin, kanamycin, and neomycin; acyclovir, famciclovir, foscarnet, ganciclovir, idoxuridine, sorivudine, trifluridine, valacylcovir, vidarabine, didanosine, stavudine, zalcitabine, zidovudine, amantadine, interferons, ribavirin, rimantadine, nucleoside RT inhibitors selected from lamivudine and adeforvir; non-nucleoside inhibitors selected from nevrapine, delavairidine, Iviride, saquinavir and indinavir; nucleoside DNAp inhibitors selected from famciclovir, fialuridine, cidofovir and lobucavir; antisense oligonucleotides; receptor decoys; capsid binding agents; neuraminidase inhibitors; cimetidine, ranitidine, captopril, methyldopa selegiline, diphenidol, meclizine hydrochloride, prochloperazine maleate, phenoxybenzamine, triethylperazine maleate, anisindone, diphenadione erythrityl tetranitrate, digoxin, isofilurophate, acetazolamide, methazolamide, bendroflumethiazide, chlorpropamide, tolazamide, chlormadionone acetate, phenaglycodol, allopurinol, alluminurri aspirin, methotrexate, acetyl sulfisoxazole, erythromyciin, progestins, estrogens, progestational corticosteroids, hydrocortisone, hydrocorticosterone acetate, cortisone acetate, tramcinolone, methyltesterone, 17-beta-estradiol, ethinyl estradiol, prazosin hydrochloride, ethinyl estradiool 3-methyl ether, prednisolone, 17-alpha-hydroxyprogesterone acetate, 19-norprogesterone, norgestrel, norethindrone, progesterone, norgesterone, norethlynodrel, cimetidine, famotidine, nizatidine, zolentine, omeprazole, lansoprazole, metronidazole, timidazole, amoxicillin, clarithromycin, minocycline, tetracycline, alfluzosin, prazosin, ketanserin, guanabenz acetate, captopril, captopril hydrochloride, enalapril, enalapril maleate, lysinopril, hydralazide, methyldopa, methyldopa hydrochloride, levodopa, carbidopa, benserazide, amlodipine, nitrendipine, nifedipine, nicardipine, and verapamil.

\* \* \* \* \*